US007435824B2

(12) United States Patent
Gross et al.

(10) Patent No.: US 7,435,824 B2
(45) Date of Patent: *Oct. 14, 2008

(54) PRODRUGS OF POTASSIUM CHANNEL INHIBITORS

(75) Inventors: Michael F. Gross, Durham, NC (US); John Lloyd, Yardley, PA (US)

(73) Assignees: Bristol-Myers Squibb Company, Princeton, NJ (US); Icagen Inc., Durham, NC (US)

( * ) Notice: Subject to any disclaimer, the term of this patent is extended or adjusted under 35 U.S.C. 154(b) by 370 days.

This patent is subject to a terminal disclaimer.

(21) Appl. No.: 11/028,399

(22) Filed: Jan. 3, 2005

(65) Prior Publication Data

US 2005/0171156 A1 Aug. 4, 2005

(51) Int. Cl.
C07D 401/02 (2006.01)
C07D 251/02 (2006.01)
A61K 31/445 (2006.01)
(52) U.S. Cl. .................. 546/207; 546/192; 514/317
(58) Field of Classification Search ................. 546/207, 546/192; 514/317
See application file for complete search history.

(56) References Cited

U.S. PATENT DOCUMENTS

| 3,097,209 | A | | 7/1963 | Janssen | |
|---|---|---|---|---|---|
| 5,612,359 | A | | 3/1997 | Murugesan | 514/365 |
| 5,631,282 | A | | 5/1997 | Goetz | 514/450 |
| 5,670,504 | A | | 9/1997 | Bochis et al. | 514/247 |
| 5,679,705 | A | | 10/1997 | Baker et al. | 514/450 |
| 5,696,156 | A | | 12/1997 | Baker et al. | 514/450 |
| 6,043,265 | A | | 3/2000 | Murugesan et al. | 514/450 |
| 6,706,720 | B2 | | 3/2004 | Atwal et al. | |
| 7,005,436 | B2 | * | 2/2006 | Lloyd et al. | 514/317 |
| 2004/0063687 | A1 | | 4/2004 | Atwal et al. | |
| 2004/0072880 | A1 | | 4/2004 | Lloyd et al. | |
| 2006/0014792 | A1 | * | 1/2006 | Lloyd et al. | 514/317 |

FOREIGN PATENT DOCUMENTS

WO WO 00/01389 1/2000
WO WO 03/088908 10/2003

OTHER PUBLICATIONS

McManus, J. M. et al., J. Medicinal Chem., vol. 8, No. 6, pp. 766-776 (1965).
Chandy and Gutman, "Voltage-gated potassium channel genes" in Handbook Receptors and Channels—Ligand and Voltage-gated Ion Channels, ed. R.A. North, 1995.
Doupnik et al., Curr. Opin. Neurobiol. 5:268, 1995.
Chandy et al., J. Exp. Med. 160, 369, 1984.
Price et al., Proc. Natl, Acad, Sci. USA, 86, 10171, 1989.
Leonard et al., Proc. Natl, Acad. Sci, USA, 89, 10094, 1992.
Lin et al., J exp. Med, 177, 637, 1993.
Singh B.N., Vaughan Williams E.M. "A Third Class of Anti-Arrhythmic Action: Effects On Atrial And Ventricular Intracellular Portentials And Other Pharmacological Actions Actions On Cardiac Muscle, of MJ 1999 and AH 3747" Br. J. Pharmacol 1970; 39:675-689.
Singh B.N., Vaughan Williams E.M, "The Effect of Amiodarone, A New Anti-Anginal Drug, On Cardiac Muscle", Br J. Pharmacol 1970; 39:657-667.
Decoursey et al., Nature, 307, 465, 1984.
Sanguinetti and Jurkiewicz, Two Components Of Cardiac Delayed Rectifier K+ Current: Differential Sensitivity To Block By Class III Antiarrhythmic Agents, J Gen Physiol 1990, 96:195-215.
Balser J.R. Bennett, P.B., Hondeghem, L.M. and Roden, D.M. Suppression Of Time-Dependent Outward Current In Guinea Pig Ventricular Myocytes: Actions Of Quinidine And Amiodarone. Circ. Res. 1991, 69:519-529.
Nademanee, K. "The Amiodarone Odessey".J.Am. Coll. Cardiol. 1992;20:1063-1065.
Roden, D.M. "Current Status of Class III Antiarrhythmic Drug Therapy", Am J. Cardiol, 1993; 72:44B-49B.
Hondeghem, L.M. "Development of Class III Antiarrhythmic Agents". J.Cadiovasc.Cardiol.20 (Suppl.2):S17-S22 (1992).
Wang et al., 1993, Circ Res 73:1061-1076.
Fedida et al., 1993, Circ Res 73:210-216.
Snyders et al., 1993, J Gen Physiol 101:513-543.
Swanson et al., (1990), Neuron 4:929-939.
Vaughn Williams, E.M. "Classification Of Antiarrhythmic Drugs" In Symposium On Cardiac Arrhythmias, edited by: E. Sandoe, E. Flensted-Jensen, K. Olesen; Sweden, Astra, Sodertalje, pp. 449-472, 1970.
Br. J. Pharmacol. May 1995;115(2):267-74.
Grissmer S, et al., Mol Pharmacol Jun. 1994;45(6):1227-34.
Petersen KR, and Nerbonne JM, Pflugers Arch Feb. 1999;437(3):381-92.
Bowlby MR, and Levitan IB, J Neurophysiol Jun. 1995;73(6):2221-9.
Kalman K, et al., J Biol Chem Mar. 6, 1998;273(10):5851-7.
Cochran et al., "Regionally selective alterations in local cerebral glucose utilization evoked by charybdotoxin, a blocker of central voltage-activated K+-channels," Eur J Neurosci. Nov. 2001;14(9):1455-63.
Coleman et al., "Subunit composition of Kv1 channels in human CNS," J Neurochem. Aug. 1999;73(2):849-58.
Davies et al., "Kv channel subunit expression in rat pulmonary arteries," Lung. 2001;179(3):147-61. Epub Feb. 4, 2002.
Frey et al., "Blocking of cloned and native delayed rectifier K channels from visceral smooth muscles by phencyclidine," Neurogastroenterol Motil. Dec. 2000;12(6):509-16.
Hanson et al., "UK-78,282, a novel piperidine compound that potently blocks the Kv1.3 voltage-gated potassium channel and inhibits human T cell activation," British Journal of Pharmacology (1999), 126, 1707-1716.

(Continued)

Primary Examiner—Rita J Desai
(74) Attorney, Agent, or Firm—Rosemary M. Miano; Terence J. Bogie

(57) ABSTRACT

Compounds useful as prodrugs of potassium channel inhibitor compounds, in particular as prodrugs of Kv1.5 channel inhibitors.

7 Claims, No Drawings

OTHER PUBLICATIONS

Hatton et al., "Functional and molecular expression of a voltage-dependent K(+) channel (Kv1.1) in interstitial cells of Cajal," J Physiol. Jun. 1, 2001;533 (Pt 2):315-27.

Koh et al., "Contribution of delayed rectifier potassium currents to the electrical activity of murine colonic smooth muscles," J Physiol. Mar. 1, 1999; 515 (Pt 2):475-87.

Kourrich et al., "Kaliotoxin, a Kv1.1 and Kv1.3 channel blocker, improves associative learning in rats," Behav Brain Res. Apr. 8, 2001;120(1):35-46.

Lopantsev et al., "Hyperexcitability of CA3 pyramidal cells in mice lacking the potassium channel subunit Kv1.1," Epilepsia. Dec. 2003;44(12):1506-12.

MacDonald et al., "Members of the Kv1 and Kv2 voltage-dependent K(+) channel families regulate insulin secretion," Mol. Endocrinol. Aug. 2001;15(8):1423-35.

MacDonald et al., "Voltage-dependant K(+) channels in pancreatic beta cells: role, regulation and potential as therapeutic targets," Diabetologia. Aug. 2003;46(8):1046-62. Epub Jun. 27, 2003.

Pozeg et al., "In vivo gene transfer of the O2-sensitive potassium channel Kv1.5 reduces pulmonary hypertension and restores hypoxic pulmonary vasoconstriction in chronically hypoxic rats," Circulation. Apr. 22, 2003;107(15):2037-44. Epub Apr. 14, 2003.

Rho et al., "Developmental seizure susceptibility of kv1.1 potassium channel knockout mice," Dev Neurosci. Nov. 1999;21(3-5):320-7.

Shah et al., "Immunosuppressive effects of a Kv1.3 inhibitor," Cellular Immunology 221, (2003), 100-106.

Vianna-Jorge et al., "Shaker-type Kv1 channel blockers increase the peristaltic activity of guinea-pig ileum by stimulating acetylcholine and tachykinins release by the enteric nervous system," Br J Pharmacol. Jan. 2003; 138(1):57-62.

Wickenden, "Potassium channels as anti-epileptic drug targets," Neuropharmacology. Dec. 2002;43(7):1055-60.

Wulff et al., "Potassium channels as therapeutic targets for autoimmune disorders," Current Opinion in Drug Discovery & Development 2003 6(5):640-647.

Xu et al., "The voltage-gated potassium channel Kv1.3 regulates peripheral insulin sensitivity," Proc Natl Acad Sci U S A. Mar. 2, 2004;101(9):3112-7. Epub Feb. 23, 2004 (epublished Feb. 23, 2004).

* cited by examiner

PRODRUGS OF POTASSIUM CHANNEL INHIBITORS

This application claims the benefit of priority from U.S. application Ser. No. 10/417,355, filed Apr. 16, 2003 now U.S. Pat. No. 7,005,436, which claims the benefit of U.S. Provisional Application Ser. No. 60/374,279 filed Apr. 19, 2002, and U.S. application Ser. No. 10/356,158 filed Jan. 31, 2003, now abandoned, which claimed benefit of U.S. Provisional application Ser. No. 60/353,884 filed Feb. 1, 2002. The entire disclosure of each of the aforementioned applications is incorporated herein by reference in its entirety.

FIELD OF APPLICABILITY OF THE INVENTION

The invention relates to compounds that function, for example, as prodrugs of piperidine compounds useful as potassium channel inhibitors, in particular those having atrial selective function for the prevention and treatment of cardiac arrhythymias. In this regard, the potassium channel inhibitors of interest are those which function as inhibitors of the $K_v1$ subfamily of voltage gated $K^+$ channels, in particular inhibitors of $K_v1.5$ channels, which have been linked to ultra-rapidly activating delayed rectifier $K^+$ current, also known as $I_{Kur}$.

BACKGROUND OF THE INVENTION

Atrial fibrillation (AF) and atrial flutter are the most common cardiac arrhythmias in clinical practice and are likely to increase in prevalence with the aging of the population. Currently, AF affects more than 1 million Americans annually, represents over 5% of all admissions for cardiovascular diseases, and causes more than 80,000 strokes each year in the United States. While AF is rarely a lethal arrhythmia, it is responsible for substantial morbidity and can lead to complications such as the development of congestive heart failure or thromboembolism. Currently available Class I and Class III antiarrhythmic drugs reduce the rate of recurrence of AF, but are of limited use because of a variety of potentially adverse effects including ventricular proarrhythmia. Because current therapy is inadequate and fraught with side effects, there is a clear need to develop new therapeutic approaches.

Antiarrhythmic agents of Class III are drugs that cause a selective prolongation of the duration of the action potential without significant cardiac depression. Available drugs in this class are limited in number. Examples such as sotalol and amiodarone have been shown to possess interesting Class III properties (Singh B. N., Vaughan Williams E. M. "A Third Class of Anti-Arrhythmic Action: Effects On Atrial And Ventricular Intracellular Potentials And Other Pharmacological Actions On Cardiac Muscle, of MJ 1999 and AH 3747" Br. J. Pharmacol 1970; 39: 675-689. and Singh B. N., Vaughan Williams E. M, "The Effect of Amiodarone, A New Anti-Anginal Drug, On Cardiac Muscle", Br J. Pharmacol 1970; 39: 657-667), but these are not selective Class III agents. Sotalol also possesses Class II effects which may cause cardiac depression and is contraindicated in certain susceptible patients. Amiodarone also is not a selective Class III antiarrhythmic agent because it possesses multiple electrophysiological actions and is severely limited by side effects (Nademanee, K. "The Amiodarone Odessey". J. Am. Coll. Cardiol. 1992; 20:1063-1065.) Drugs of this class are expected to be effective in preventing ventricular fibrillation. Selective class III agents, by definition, are not considered to cause myocardial depression or an induction of arrhythmias due to inhibition of conduction of the action potential as seen with Class I antiarrhythmic agents.

Class III agents increase myocardial refractoriness via a prolongation of cardiac action potential duration. Theoretically, prolongation of the cardiac action potential can be achieved by enhancing inward currents (i.e. $Na^+$ or $Ca^{2+}$ currents; hereinafter $I_{Na}$ and $I_{Ca}$, respectively) or by reducing outward repolarizing potassium ($K^+$) currents. The delayed rectifier ($I_K$) $K^+$ current is the main outward current involved in the overall repolarization process during the action potential plateau, whereas the transient outward ($I_{to}$) and inward rectifier ($I_{KI}$) $K^+$ currents are responsible for the rapid initial and terminal phases of repolarization, respectively. Cellular electrophysiologic studies have demonstrated that $I_K$ consists of three pharmacologically and kinetically distinct $K^+$ current subtypes, $I_{Ku}$ (rapidly activating and deactivating) and $I_{Ks}$ (slowly activating and deactivating) (Sanguinetti and Jurkiewicz, Two Components Of Cardiac Delayed Rectifier $K^+$ Current: Differential Sensitivity To Block By Class III Antiarrhythmic Agents, J Gen Physiol 1990, 96:195-215). In addition, the ultra-rapidly activating $K^+$ $I_{Kur}$ current is believed to represent the native counterpart to a cloned potassium channel, designated as Kv1.5. While present in the human atrium, it appears to be absent from the human ventricle. Because it is rapidly activating and because of the correspondingly limited slow inactivation, $I_{Kur}$ is believed to contribute significantly to repolarization in the human atrium. Consequently, an agent that specifically blocks $I_{Kur}$ would prolong refractoriness and retard repolarization of the human atrium in the event of a cardiac arrhythmia, yet at the same time not cause delays in ventricular repolarization. As a result, arrythymogenic after-depolarizations, and acquired long QT syndrome that is observed during treatment with conventional class III antiarrhythmic agents could also be avoided. The effect of $I_{Kur}$ in retarding repolarization of the human atrium would also be preventive to the occurrence of atrial fibrillations and arrhythmias.

In intact human atrial myocytes an ultra-rapidly activating delayed rectifier $K^+$ Current $I_{Kur}$ which is also known as the sustained outward current, $I_{sus}$ or $I_{so}$, has been identified and this current has properties and kinetics identical to those expressed by the human $K^+$ channel clone (hKv1.5, HK2) when isolated from human heart and stably expressed in human (HEK-293) cell lines. (Wang et al., 1993, Circ Res 73: 1061-1076; Fedida et al., 1993, Circ Res 73: 210-216; Snyders et al., 1993, J Gen Physioi 101: 513-543) and originally cloned from rat brain (Swanson et al., 10, Neuron 4: 929-939). Although various antiarrythmic agents are now available on the market, those having both satisfactory efficacy and a high margin of safety have not been obtained. For example, antiarrythmic agents of Class I according to the classification scheme of Vaughan-Williams ("Classification Of Antiarrhythmic Drugs: In: Cardiac Arrhythmias, edited by: E. Sandoe, E. Flensted-Jensen, K. Olesen; Sweden, Astra, Sodertalje, pp 449-472, 1981) which cause a selective inhibition of the maximum velocity of the upstroke of the action potential ($V_{max}$) are inadequate for preventing ventricular fibrillation. In addition, they have problems regarding safety, namely, they cause a depression of myocardial contractility and have a tendency to induce arrhythmias due to an inhibition of impulse conduction. Beta-adrenoceptor blockers and calcium antagonists which belong to Class II and IV, respectively, have a defect in that their effects are either limited to a certain type of arrhythmia or are contraindicated because of their cardiac depressant properties in certain patients with cardiovascular disease. Their safety, however, is higher than that of the antiarrhythmic agents of Class I.

Immunoregulatory abnormalities have been shown to exist in a wide variety of autoimmune and chronic inflammatory diseases, including systemic lupus erythematosis, chronic rheumatoid arthritis, type I and II diabetes mellitus, inflammatory bowel disease, biliary cirrhosis, uveitis, multiple sclerosis and other disorders such as Crohn's disease, ulcerative colitis, bullous pemphigoid, sarcoidosis, psoriasis, ichthyosis, Graves ophthalmopathy and asthma. Although the underlying pathogenesis of each of these conditions may be quite different, they have in common the appearance of a variety of auto-antibodies and self-reactive lymphocytes. Such self-reactivity may be due, in part, to a loss of the homeostatic controls under which the normal immune system operates. Similarly, following a bone-marrow or an organ transplantation, the host lymphocytes recognize the foreign tissue antigens and begin to produce antibodies which lead to graft vs. host rejection.

One end result of an autoimmune or a rejection process is tissue destruction caused by inflammatory cells and the mediators they release. Anti-inflammatory agents such as NSAID's act principally by blocking the effect or secretion of these mediators but do nothing to modify the immunologic basis of the disease. On the other hand, cytotoxic agents, such as cyclophosphamide, act in such a nonspecific fashion in which both the normal and autoimmune responses are shut off. Indeed, patients treated with such nonspecific immunosuppressive agents are as likely to succumb to infection as they are to their autoimmune disease.

Cyclosporin A, which was approved by the US FDA in 1983 is currently the leading drug used to prevent rejection of transplanted organs. In 1993, FK-506 (Prograf) was approved by the US FDA for the prevention of rejection in liver transplantation. Cyclosporin A and FK-506 act by inhibiting the body's immune system from mobilizing its vast arsenal of natural protecting agents to reject the transplant's foreign protein. In 1994, Cyclosporin A was approved by the US FDA for the treatment of severe psoriasis and has been approved by European regulatory agencies for the treatment of atopic dermatitis. Though these agents are effective in fighting transplant rejection, Cyclosporin A and FK-506 are known to cause several undesirable side effects including nephrotoxicity, neurotoxicity, and gastrointestinal discomfort. Therefore, a selective immunosuppressant without these side effects still remains to be developed. Potassium channel inhibitors as described here promise to be the solution to this problem, since inhibitors of Kv1.3, for example, are immunosuppressive. See, Wulff et al., "Potassium channels as therapeutic targets for autoimmune disorders," Curr Opin Drug Discov Devel. 2003 September; 6(5):640-7; Shah et al., "Immunosuppressive effects of a Kv1.3 inhibitor," Cell Immunol. 2003 February; 221(2):100-6; Hanson et al., "UK-78,282, a novel piperidine compound that potently blocks the Kv1.3 voltage-gated potassium channel and inhibits human T cell activation," Br J Pharmacol. 1999 April; 126(8):1707-16.

Inhibitiors of Kv1.5 and other Kv1.x channels stimulate gastrointestinal motility. Thus, the compounds of the invention are believed to be useful in treating motility disorders such as reflux esophagitis. See, Frey et al., "Blocking of cloned and native delayed rectifier K channels from visceral smooth muscles by phencyclidine," Neurogastroenterol Motil. 2000 December; 12(6): 509-16; Hatton et al., "Functional and molecular expression of a voltage-dependent K(+) channel (Kv1.1) in interstitial cells of Cajal," J. Physiol. 2001 Jun. 1; 533 (Pt 2): 315-27; Vianna-Jorge et al., "Shaker-type Kv1 channel blockers increase the peristaltic activity of guinea-pig ileum by stimulating acetylcholine and tachykinins release by the enteric nervous system," Br J Pharmacol. 2003 January; 138(1): 57-62; Koh et al., "Contribution of delayed rectifier potassium currents to the electrical activity of murine colonic smooth muscle," J. Physiol. 1999 Mar. 1; 515 (Pt 2):475-87.

Inhibitors of Kv1.5 relax pulmonary artery smooth muscle. Thus, the compounds of the invention are believed to be useful in treating hypertension and otherwise improving vascular health. See, Davies et al., "Kv channel subunit expression in rat pulmonary arteries," Lung. 2001; 179(3): 147-61. Epub 2002 Feb. 04; Pozeg et al., "In vivo gene transfer of the $O_2$-sensitive potassium channel Kv1.5 reduces pulmonary hypertension and restores hypoxic pulmonary vasoconstriction in chronically hypoxic rats," Circulation. 2003 Apr. 22; 107(15):2037-44. Epub 2003 Apr. 14.

Inhibitors of Kv1.3 increase insulin sensitivity. Hence, the compounds of the invention are believed to be useful in treating diabetes. See, Xu et al., "The voltage-gated potassium channel Kv1.3 regulates peripheral insulin sensitivity," Proc Natl Acad Sci USA. 2004 Mar. 2; 101 (9): 3112-7. Epub 2004 Feb. 23 (epublished 2004 Feb. 23); MacDonald et al., "Members of the Kv1 and Kv2 voltage-dependent K(+) channel families regulate insulin secretion," Mol Endocrinol. 2001 Aug.; 15(8): 1423-35; MacDonald et al., "Voltage-dependent K(+) channels in pancreatic beta cells: role, regulation and potential as therapeutic targets," Diabetologia. 2003 August; 46(8):1046-62. Epub 2003 Jun. 27.

Stimulation of Kv1.1 is believed to reduce seizure activity by hyperpolarizing neurons. Thus, the compounds of the invention are believed to be useful in treating seizures, including seizures associated with epilepsy and other neurological diseases. See, Rho et al., "Developmental seizure susceptibility of kv1.1 potassium channel knockout mice," Dev Neurosci. 1999 Nov.; 21(3-5): 320-7; Coleman et al., "Subunit composition of Kv1 channels in human CNS," J. Neurochem. 1999 August; 73(2): 849-58; Lopantsev et al., "Hyperexcitability of CA3 pyramidal cells in mice lacking the potassium channel subunit Kv1.1," Epilepsia. 2003 December; 44(12): 1506-12; Wickenden, "Potassium channels as anti-epileptic drug targets," Neuropharmacology. 2002 December; 43(7): 1055-60.

Inhibition of Kv1.x channels improves cognition in animal models. Thus, the compounds of the invention are believed to be useful in improving cognition and/or treating cognitive disorders. See, Cochran et al., "Regionally selective alterations in local cerebral glucose utilization evoked by charybdotoxin, a blocker of central voltage-activated K+-channels," Eur J Neurosci. 2001 November; 14(9): 1455-63; Kourrich et al., "Kaliotoxin, a Kv1.1 and Kv1.3 channel blocker, improves associative learning in rats," Behav Brain Res. 2001 Apr. 8; 120(1): 35-46.

Based on the foregoing discussion, there is evident in the art a recognized need for pharmaceutical substances belonging to the $K_v1.5$ subfamily of potassium channel inhibitors that may be used as therapeutic agents, particularly atrial selective thereapeutic agents, in the prevention and treatment of cardiac arrhythymias. Such compounds by virtue of the observed link between $K_v1.5$ function and other indications as discussed above, would also prove to be useful in a wide range of therapeutic treatment applications associated with $K_v1.3$ immunoregulatory function. In addition, blockers and activators of $K_v1.x$ channels could be expected to have the utilities described above.

SUMMARY OF THE INVENTION

The present invention provides compounds according to the formula I:

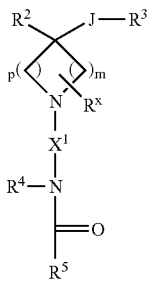

including enantiomers, diastereomers, solvates and salts thereof, wherein $X^1$ is selected from

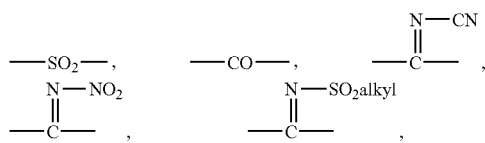

—C=N(CO$_2$alkyl)- and —C=N(COalkyl)-;

m and p are independently 0, 1, 2 or 3, provided that both m and p cannot be 0;

J is a bond or $C_{1-4}$ alkylene;

$R^2$ is heterocyclo, (heteroaryl)alkyl, aryl, (aryl)alkyl, (heterocyclo)alkyl, alkyl or cycloalkyl, any of which may be optionally independently substituted with one or more groups $T^1$, $T^2$ or $T^3$;

$R^4$ is selected from H, alkyl, cycloalkyl, heterocyclo, heteroalkyl or aryl, any of which may be substituted with one or more groups $T^1$, $T^2$ or $T^3$;

$R^5$ is selected from alkyl, heteroalkyl, aryl, or heterocyclo, any of which may be substituted with one or more groups $T^1$, $T^2$ or $T^3$;

$R^3$ is selected from

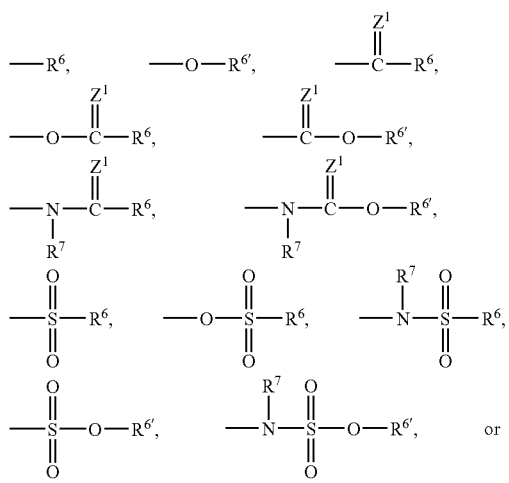

-continued

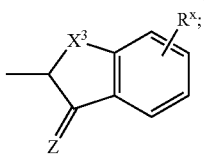

wherein $Z^1$ is selected from O, S or $NR^{13}$; where $R^{13}$ is hydrogen, alkyl, CN, $NO_2$, $SO_2$alkyl, $CO_2$alkyl or COalkyl;

$X^3$ is selected from —O—, —S— or —NH;

$R^6$ is selected from —$NR^8R^9$, -alkyl-$NR^8R^9$, $C_{1-6}$ alkyl or substituted $C_{1-6}$ alkyl, aryl, heteroaryl, cycloalkyl, or heterocyclo, each of which may be independently substituted with one or more groups $T^1$, $T^2$, or $T^3$;

$R^{6'}$ is selected from $C_{1-6}$ alkyl or substituted $C_{1-6}$ alkyl, aryl, heteroaryl, cycloalkyl, or heterocyclo, each of which may be independently substituted with one or more groups $T^1$, $T^2$, or $T^3$;

$R^7$, $R^8$, and $R^9$ are each independently selected from H, alkyl, hydroxy, alkoxy, aryloxy, heterocyclooxy, heteroaryloxy, (hydroxy)alkyl, (alkoxy)alkyl, (aryloxy)alkyl, (heterocyclooxy)alkyl, (heteroaryloxy)alkyl, (cyano)alkyl, (alkenyl) alkyl, (alkynyl)alkyl, cycloalkyl, (cycloalkyl)alkyl, aryl, (aryl)alkyl, heteroaryl, (heteroaryl)alkyl, heterocyclo, (heterocyclo)alkyl, —C(O)$R^{10}$, —$CO_2R^{10}$, —C(O)—$NR^{10}R^{11}$, or any of which may be optionally independently substituted with one or more groups $T^1$, $T^2$ or $T^3$;

$R^{10}$ and $R^{11}$ are each independently selected from H, alkyl, hydroxy, alkoxy, aryloxy, heterocyclooxy, heteroaryloxy, (hydroxy)alkyl, (alkoxy)alkyl, (aryloxy)alkyl, (heterocyclooxy)alkyl, (heteroaryloxy)alkyl, cycloalkyl, (cycloalkyl)alkyl, aryl, (aryl)alkyl, heteroaryl, (heteroaryl)alkyl, heterocyclo, or (heterocyclo)alkyl any of which may be optionally independently substituted with one or more groups $T^1$, $T^2$ or $T^3$;

or $R^{10}$ and $R^{11}$ together with the nitrogen atom to which they are attached may combine to form a saturated or unsaturated ring which may be independently substituted with one or more groups $T^1$, $T^2$ or $T^3$;

$R^x$ is one or more optional substituents, attached to any available ring carbon atom, each of which is independently selected from $T^1$, $T^2$ or $T^3$;

$T^1$, $T^2$ and $T^3$ are each independently selected from (1) hydrogen, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl, (heteroaryl)alkyl, —$OR^{12}$, —S $R^{12}$, —CHO, —COOH, —COO $R^{12}$, —OCO—$R^{12}$, —CO—$R^{12}$, —CON($R^{12}$)($R^{12}$), —$CONH_2$, —$SONH_2$, —$SO_2NH_2$, —$NH_2$, —$SO_3H$, —$SO_2$—$R^{12}$, —$SO_2$—N—($R^{12}$)($R^{12}$), —N($R^{12}$)($R^{12}$) or $CF_3$;

(2) —OH;

(3) —SH;

(4) halo, (5) cyano, and (6) nitro;

$R^{12}$ is selected from alkyl, cycloalkyl, heterocyclo, aryl or heteroaryl, each of which may be independently substituted with one or more groups $T^1$, $T^2$ or $T^3$.

Exemplary compounds of formula I are those according to the formulae Ia and Ib:

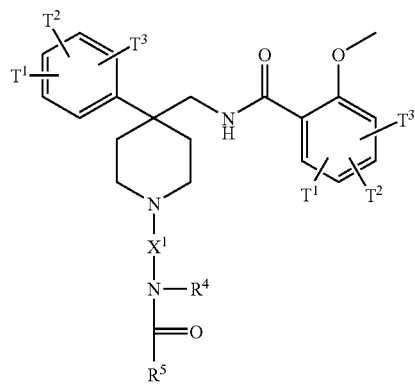
(Ia)

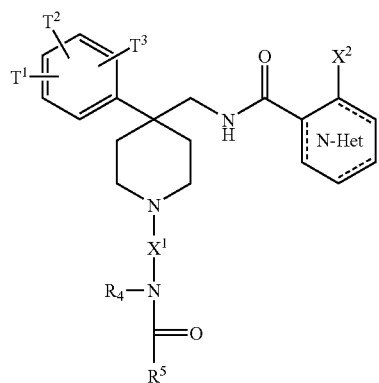
(Ib)

wherein $T^1$, $T^2$, $T^3$, $R^4$, $R^5$ and $X^1$, are as defined hereinabove; $X^2$ is selected from —$C_{1-4}$alkyl or —O—$C_{1-4}$alkyl or amino, and the heterocyclic ring N-Het is as defined herein below.

Other preferred compounds according to the invention are those of formula I wherein wherein $R^5$ is -alkyl($NR^{15}R^{16}$), where $R^{15}$ and $R^{16}$ are each independently selected from H, alkyl, heteroalkyl, aryl, heteroaryl; or $R^{15}$ and $R^{16}$, taken together with the nitrogen atom to which they are attached form a 4-8-membered heterocyclic ring.

The compounds according to Formula I behave as prodrugs and are metabolized in vivo to provide compounds useful as inhibitors of potassium channel function (especially inhibitors of the $KV_1$ subfamily of voltage gated $K^+$ channels, more especially inhibitors $K_v1.5$ which has been linked to the ultra-rapidly activating delayed rectifier $K^+$ current $I_{Kur}$).

The invention further comprises pharmaceutical compositions comprising a therapeutically effective amount of at least one compound described herein and a pharmaceutically acceptable vehicle or carrier thereof. Such compositions can further comprise at least one other anti-arrhythmic agent (such as sotalol, dofetilide, diltiazem or Verapamil), or at least one calcium channel blocker, or at least one anti-platelet agent (such as clopidogrel, cangrelor, ticlopidine, CS-747, ifetroban and aspirin), or at least one anti-hypertensive agent (such as a beta adrenergic blocker, ACE inhibitor (e.g., captopril, zofenopril, fosinopril, enalapril, ceranopril, cilazopril, delapril, pentopril, quinapril, ramipril, or lisinopril), A II antagonist, ET antagonist, Dual ET/A II antagonist, or vasopepsidase inhibitor (e.g., omapatrilat or gemopatrilat)), or at least one anti thrombotic/anti thrombolytic agent (such as tPA, recombinant tPA, TNK, nPA, factor VIIa inhibitors, factor Xa inhibitors (such as razaxaban), factor XIa inhibitors or thrombin inhibitors), or at least one anti coagulant (such as warfarin or a heparin), or at least one HMG-CoA reductase inhibitor (pravastatin, lovastatin, atorvastatin, simvastatin, NK-104 or ZD-4522), or at least one anti diabetic agent (such as a biguanide or a biguanide/glyburide combination), or at least one thyroid mimetic, or at least one mineralocorticoid receptor antagonist (such as spironolactone or eplerinone), or at least one cardiac glycoside (such as digitalis or ouabain).

The invention additionally includes use of a compound according to the invention, optionally in combination with one or more other pharmaceutical agents and or carriers as described above, in methods of treating (including preventing or ameliorating) arrhythmias, atrial fibrillation, atrial flutter, supraventricular arrhythymias, gastrointestinal disorders (such as reflux esophagitis or a motility disorder), inflammatory or immunological disease (such as chronic obstructive pulmonary disease), diabetes, cognitive disorders, migraine, epilepsy, hypertension, or treating $I_{Kur}$-associated conditions, or controlling heart rate.

The invention further comprises a method of preparing compounds according to Scheme I.

In addition, the invention comprises a method for providing a physiologically effective amount of a potassium channel inhibitor to a mammalian subject comprising administering a therapeutically effective amount of a compound according to the formula I, optionally in combination with a therapeutically effective amount of at least one other pharmaceutical agent as described above.

DETAILED DESCRIPTION

The compounds according to the invention have utility, inter alia, as prodrugs of potassium channel inhibitor compounds that may be used to treat various physiological indications. In particular compounds according to formula I are metabolized in vivo to provide potassium channel inhibitor compounds. Salts and solvates of the compounds of the invention are also contemplated herein. The term "prodrug" denotes a compound which, upon administration to a subject, undergoes chemical conversion by metabolic or chemical processes to yield a compound of the formula II, or a salt and/or solvate thereof. Solvates of the compounds of formula II can be hydrates.

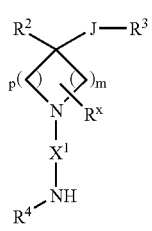
II

Exemplary such compounds of the formula II, are those, for example, according to formula IIa and IIb

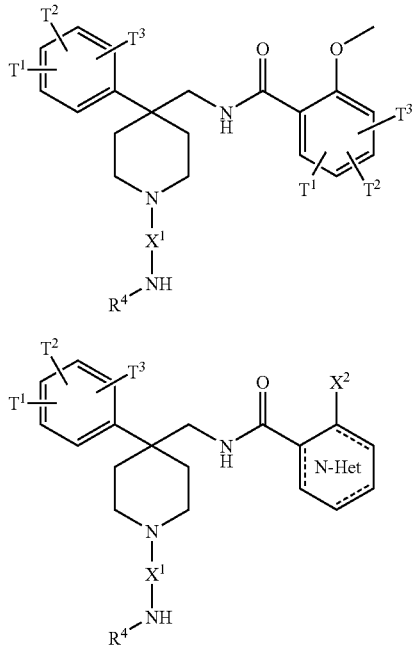

wherein $T^1$, $T^2$, $T^3$, $R^4$ and $X^1$, are as defined hereinabove;
$X^2$ is selected from —$C_{1-4}$alkyl or —O—$C_{1-4}$alkyl or amino, and the heterocyclic ring N-Het is as defined herein below.

Compounds according to Formula I may be prepared according to the general scheme 1 shown herein below.

The terms "alk," "alkyl," and "alkylene" refer to straight or branched chain hydrocarbon groups or radicals having 1 to 12 carbon atoms, or 1 to 8 carbon atoms, such as methyl, ethyl, n-propyl, i-propyl, n-butyl, i-butyl, t-butyl, pentyl, hexyl, heptyl, octyl, carbocycles having 3 to 8 carbon atoms, or any subset of the foregoing, any of which may be optionally substituted with one or more groups, for example those described herein in the definition of the substituents $T^1$, $R^1$ or $R^3$. Lower alkyl groups, that is, alkyl groups of 1 to 6 carbon atoms, are generally most preferred. The term "alkyl" also includes the term "substituted alkyl," which refers to alkyl groups substituted with one or more groups (such as by groups described above in the definition of $T^1$), such as selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane and sulfonyl, or any subset of the foregoing.

The term "alkenyl" refers to straight or branched chain hydrocarbon groups having 2 to 12 carbon atoms, or 2 to 4 carbon atoms, and at least one double carbon to carbon bond (either cis or trans), such as ethenyl. The term "alkynyl" also includes the term "substituted alkenyl," which refers to alkenyl groups substituted with one or more groups (such as by groups described above in the definition of $T^1$), such as selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane and sulfonyl, or any subset of the foregoing.

The term "alkynyl" refers to straight or branched chain hydrocarbon groups having 2 to 12 carbon atoms, or 2 to 4 carbon atoms, and at least one triple carbon to carbon bond, such as ethynyl. The term "alkynyl" also includes "substituted alkynyl," which refers to alkynyl groups substituted with one or more groups (such as by groups described above in the definition of $T^1$), such as selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane and sulfonyl, or any subset of the foregoing.

The terms "alkylester" or "alkyl ester" mean alkyl-CO—O-alkyl or alkyl-O—CO-alkyl. The term "arylester" means aryl-CO—O-alkyl or aryl-O—CO-alkyl.

The terms "ar" or "aryl" refer to aromatic homocyclic (i.e., hydrocarbon) mono-, bi- or tricyclic ring-containing groups such as those having 6 to 12 members, for example phenyl, naphthyl and biphenyl. Phenyl is a preferred aryl group. The terms "ar" or "aryl" also include "substituted aryl," which term refers to aryl groups substituted with one or more groups (such as the groups described above in the definition of $T^1$), such as selected from alkyl, substituted alkyl, alkenyl (optionally substituted), aryl (optionally substituted), heterocyclo (optionally substituted), halo, hydroxy, alkoxy (optionally substituted), aryloxy (optionally substituted), alkanoyl (optionally substituted), aroyl, (optionally substituted), alkylester (optionally substituted), arylester (optionally substituted), cyano, nitro, amino, substituted amino, amido, lactam, urea, urethane and sulfonyl, or any subset of the foregoing, where optionally one or more pair of substituents together with the atoms to which they are bonded form a 3 to 7 member ring.

The terms "cycloalkyl" and "cycloalkenyl" refer to mono-, bi- or tri homocyclic ring groups of 3 to 15 carbon atoms which are, respectively, fully saturated and partially unsaturated. The term "cycloalkenyl" includes bi- and tricyclic ring systems that are not aromatic as a whole, but contain aromatic portions (e.g. fluorene, tetrahydronapthalene, dihydroindene, and the like). The rings of multi-ring cycloalkyl groups may be either fused, bridged and/or joined through one or more spiro unions. The terms "cycloalkyl" and "cycloalkenyl" also include "substituted cycloalkyl" and "substituted cycloalkenyl," which refer, respectively, to cycloalkyl and cycloalkenyl groups substituted with one or more groups (such as by groups described above in the definitions of $T^1$, $R^1$ or $R^3$), or such as may be selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryloyl (optionally substituted), cyano, nitro, amino, substituted amino, amido, lactam, urea, urethane and sulfonyl, or any subset of the foregoing.

The terms "carbocyclo", "carbocyclic" or "carbocyclic group" refer to both cycloalkyl and cycloalkenyl groups. The terms "carbocyclo", "carbocyclic" also include "substituted carbocyclo", "substituted carbocyclic" or "substituted carbocyclic group," which all refer to carbocyclo or carbocyclic groups substituted with one or more groups as described in the definition of cycloalkyl and cycloalkenyl.

The terms "halogen" and "halo" refer to fluorine, chlorine, bromine and iodine.

The terms "heterocycle", "heterocyclic", "heterocyclic group" or "heterocyclo" refer to fully saturated or partially or completely unsaturated, including aromatic ("heteroaryl") or nonaromatic substituted or unsubstituted cyclic groups (for example, 3 to 13 ring member monocyclic, 7 to 17 ring member bicyclic, or 10 to 20 ring member tricyclic ring systems, such as, in certain embodiments, a monocyclic or bicyclic ring containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system. The rings of multi-ring heterocycles may be either fused, bridged and/or joined through one or more spiro unions.

Exemplary monocyclic heterocyclic groups include azetidinyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridyl, pyrazinyl, pyrimidinyl, pyridazinyl, triazinyl, tetrahydropyranyl, tetrazoyl, triazolyl, morpholinyl, thiamorpholinyl, thiamorpholinyl sulfoxide, thiamorpholinyl sulfone, 1,3-dioxolane and tetrahydro-1,1-dioxothienyl,

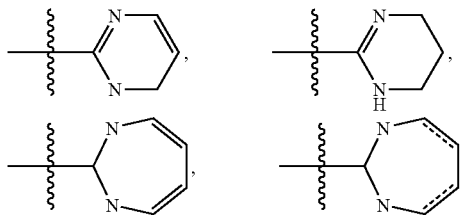

and the like.

Exemplary bicyclic heterocyclic groups include indolyl, benzothiazolyl, benzoxazolyl, benzothienyl, quinuclidinyl, quinolinyl, tetra-hydroisoquinolinyl, isoquinolinyl, benzimidazolyl, benzopyranyl, indolizinyl, benzofuryl, benzofuranly, dihydrobenzofuranyl, chromonyl, coumarinyl, benzodioxolyl, dihydrobenzodioxolyl, benzodioxinyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), tetrahydroquinolinyl, azabicycloalkyls (such as 6-azabicyclo[3.2.1]octane), azaspiroalkyls (such as 1,4 dioxa-8-azaspiro[4.5]decane), imidazopyridinyl (such as imidazo[1,5-a]pyridin-3-yl), triazolopyridinyl (such as 1,2,4-triazolo[4,3-a]pyridin-3-yl), and hexahydroimidazopyridinyl (such as 1,5,6,7,8,8a-hexahydroimidazo[1,5-a]pyridin-3-yl),

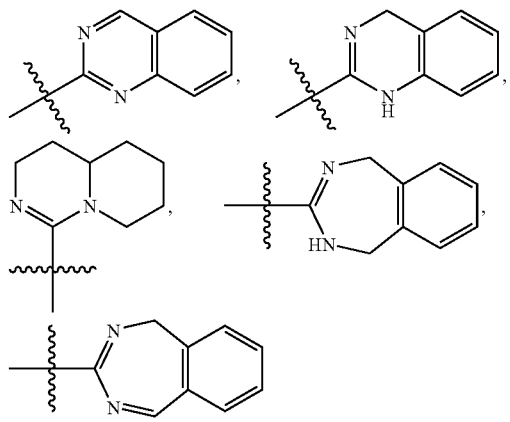

and the like.

Exemplary tricyclic heterocyclic groups include carbazolyl, benzidolyl, phenanthrolinyl, acridinyl, phenanthridinyl, xanthenyl and the like.

The term "heteroalkyl" means an alkyl group or radical consisting of 1 to 12 carbon atoms and at least one heteroatom selected from O, N and S, wherein the nitrogen and sulfur atoms may optionally be oxidized and the nitrogen heteroatom may optionally be quaternized. The heteroatom(s) may be placed at any interior position of the heteroalkyl group or at the position at which the alkyl group is attached to the remainder of the molecule. Examples include, but are not limited to, —$CH_2CH_2OCH_3$, —$CH_2CH_2NH_2$, —$CH_2CH_2N(H)CH_3$, —$CH_2CH_2N(CH_3)CH_3$, —$CH_2CH_2SCH_3$, —$CH_2CH_2S(O)_2CH_3$, —$OCH_3$, —$N(H)CH_3$, —$N(CH_3)CH_3$ and —$SCH_3$.

The term "heterocyclo" also includes the terms "substituted heterocycle", "substituted heterocyclic", "substituted heterocyclic group" and "substituted heterocyclo" refer to heterocycle, heterocyclic and heterocyclo groups substituted with one or more groups (such as by groups described above in the definition of $T^1$, $R^1$ or $R^3$), for example such as may be selected from alkyl, substituted alkyl, alkenyl, oxo, aryl, substituted aryl, heterocyclo, substituted heterocyclo, carbocyclo (optionally substituted), halo, hydroxy, alkoxy (optionally substituted), aryloxy (optionally substituted), alkanoyl (optionally substituted), aroyl (optionally substituted), alkylester (optionally substituted), arylester (optionally substituted), cyano, nitro, amido, amino, substituted amino, lactam, urea, urethane, sulfonyl, or any subset of the foregoing, where optionally one or more pair of substituents together with the atoms to which they are bonded form a 3 to 7 member ring. The designation

refers to a six-membered partially or fully saturated or unsaturated monocyclic heterocycle having one or more N atoms at any ring position.

The term "alkanoyl" refers to alkyl group (which may be optionally substituted as described above) linked to a carbonyl group (i.e. —C(O)-alkyl). Similarly, the term "aroyl"

refers to an aryl group (which may be optionally substituted as described above) linked to a carbonyl group (i.e., —C(O)-aryl).

The term "amino" means —NR$^a$R$^b$ wherein R$^a$ and R$^b$ are independently selected from H, alkyl, cycloalkyl, aryl or heterocyclo; or R$^a$ and R$^b$ taken together with the nitrogen atom to which they are attached form a 3- to 8-membered heterocyclic ring.

Throughout the specification, groups and substituents thereof may be chosen to provide stable moieties and compounds.

The compounds of formula I form salts or solvates which are also within the scope of this invention. Reference to a compound of the formula I herein is understood to include reference to salts and solvates thereof unless otherwise indicated. The term "salt(s)", as employed herein, denotes acidic and/or basic salts formed with inorganic and/or organic acids and bases. In addition, when a compound of formula I contains both a basic moiety and an acidic moiety, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of the formula I may be formed, for example, by reacting a compound I with an amount of acid or base, such as an equivalent amount, in a medium such as one in which the salt precipitates or in an aqueous medium followed by lyophilization.

The compounds of formula I which contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The compounds of formula I which contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine and the like.

Basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

To the extent that compounds of the formula 1, and salts thereof, may exist in their tautomeric form, all such tautomeric forms are contemplated herein as part of the present invention.

All stereoisomers of the present compounds, such as those which may exist due to asymmetric carbons on the various substituents, including enantiomeric forms (which may exist even in the absence of asymmetric carbons) and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations.

The terms "including", "such as", "for example" and the like are intended to refer to exemplary embodiments and not to limit the scope of the present invention.

The compounds of the invention are metabolized in vivo to provide the pharmaceutically active species. A non-limiting example of such metabolism may be hydrolysis of reactive substituents, e.g. N-acyl groups, as is described by Larsen et al., Int J Pharmaceutics 1987; 37:87-95, which is herein incorporated by reference in its entirety. This reference also describes methods of determining degradation of sulfonamide derivatives using reversed phase HPLC. Rao et al., Biopharm & Drug Disposition 2002; 23:283-282, also herein incorporated by reference in its entirety, describes the synthesis of prodrugs as acylated species using acid anhydrides and base, the products being amenable to salt formation. Single dose pharmacokinetics was measured after administration to Sprague-Dawley rats by HPLC analysis of plasma recovered from whole blood samples.

The compounds formed according to the invention are useful as prodrugs of potassium channel inhibitors (especially inhibitors of the K$_v$1 subfamily of voltage gated K$^+$ channels, more especially inhibitors K$_v$1.5 which has been linked to the ultra-rapidly activating delayed rectifier K$^+$ current I$_{Kur}$), and may be included in pharmaceutical compositions containing such compounds. Other uses for these compounds may extend to the treatment of immunoregulatory abnormalities, including a wide variety of autoimmune and chronic inflammatory diseases. Examples of these include systemic lupus erythematosis, chronic rheumatoid arthritis, type I and II diabetes mellitus, inflammatory bowel disease, biliary cirrhosis, uveitis, multiple sclerosis and other disorders such as Crohn's disease, ulcerative colitis, bullous pemphigoid, sarcoidosis, psoriasis, ichthyosis, Graves ophthalmopathy and asthma.

Compounds within the scope of the present invention are prodrugs that release compounds which inhibit the Kv1 subfamily of voltage-gated K$^+$ channels, and as such are useful in the treatment and/or prevention of various disorders: cardiac arrhythmias, including supraventricular arrhythmias, atrial arrhythmias, atrial flutter, atrial fibrillation, complications of cardiac ischemia, and use as heart rate control agents; angina pectoris including relief of Prinzmetal's symptoms, vasospastic symptoms and variant symptoms; gastrointestinal disorders including reflux esauphagitis, functional dispepsia, motility disorders (including constipation and diarrhea), and irritable bowel syndrome; disorders of vascular and visceral smooth muscle including asthma, chronic obstructive pulmonary disease, adult respiratory distress syndrome, peripheral vascular disease (including intermittent claudication), venous insufficiency, impotence, cerebral and coronary spasm and Raynaud's disease; inflammatory and immunological disease including inflammatory bowel disease, rheumatoid arthritis, graft rejection, asthma. chronic obstructive pulmonary disease, cystic fibrosis and atherosclerosis; cell poliferative disorders including restenosis and cancer (including leukemia); disorders of the auditory system; disorders of the visual system including macular degeneration and cataracts; diabetes including diabetic retinopathy, diabetic nephropathy and diabetic neuropathy; muscle disease including myotonia and wasting; peripheral neuropathy; cognitive disorders; migraine; memory loss including Alzheimer's and dementia; CNS mediated motor dysfunction including Parkinson's disease, and ataxia; epilepsy; and other ion channel mediated disorders.

As prodrug compounds that release inhibitors of the Kv1 subfamily of voltage-gated K⁺ channels compounds of the present invention are useful to treat a variety of further disorders including resistance by transplantation of organs or tissue, graft-versus-host diseases brought about by medulla ossium transplantation, rheumatoid arthritis, systemic lupus erythematosus, Hashimoto's thyroiditis, multiple sclerosis, myasthenia gravis, type I diabetes uveitis, juvenile-onset or recent-onset diabetes mellitus, posterior uveitis, allergic encephalomyelitis, glomerulonephritis, infectious diseases caused by pathogenic microorganisms, inflammatory and hyperproliferative skin diseases, psoriasis, atopical dermatitis, contact dermatitis, eczematous dermatitises, seborrheic dermatitis, Lichen planus, Pemphigus, bullous pemphigoid, Epidermolysis bullosa, urticaria, angioedemas, vasculitides, erythemas, cutaneous eosinophilias, acne, Alopecia greata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer Scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns and leukotriene B4-mediated diseases, Coeliaz diseases, proctitis, eosinophilic gastroenteritis, mastocytosis, Crohn's disease, ulcerative colitis, migraine, rhinitis, eczema, interstitial nephritis, Good-pasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idopathic interstitial pneumonia, dermatomyositis, leukoderma vulgaris, ichthyosis vulgaris, photoallergic sensitivity, cutaneous T cell lymphoma, arteriosclerosis, atherosclerosis, aortitis syndrome, polyarteritis nodosa, myocardosis, scieroderma, Wegener's granuloma, Sjogren's syndrome, adiposis, eosinophilic fascitis, lesions of gingiva, periodontium, alveolar bone, substantia osses dentis, glomerulonephritis, male pattern alopecia or alopecia senilis by preventing epilation or providing hair germination and/or promoting hair generation and hair growth, muscular dystrophy; Pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis, pigentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenis, metastatis of carcinoma and hypobaropathy, disease caused by histamine or leukotriene-C4 release, Behcet's disease, autoimmune hepatitis, primary biliary cirrhosis sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augention of chemotherapeutic effect, cytomegalovirus infection, HCMV infection, AIDS, cancer, senile dementia, trauma, and chronic bacterial infection.

The compounds of the present invention behave as prodrugs of compounds that are antiarrhythmic agents which are useful in the prevention and treatment (including partial alleviation or cure) of arrhythmias. As inhibitors of Kv1.5 or prodrugs that release compounds that are inhibitors of Kv1.5, compounds within the scope of the present invention are particularly useful in the selective prevention and treatment of supraventricular arrhythmias such as atrial fibrillation, and atrial flutter. By "selective prevention and treatment of supraventricular arrhythmias" is meant the prevention or treatment of supraventricular arrhythmias wherein the ratio of the prolongation of the atrial effective refractory period to the prolongation of the ventricular effective refractory period is greater than 1:1. This ratio is preferably greater than 4:1, more preferably greater than 10:1, and most preferably such that prolongation of the atrial effective refractory response period is achieved without significantly detectable prolongation of the ventricular effective refractory period.

In addition, the compounds within the scope of the present invention may function as prodrugs that release compounds that block $I_{Kur}$, and thus may be useful in the prevention and treatment of several $I_{Kur}$-associated conditions. An "$I_{Kur}$-associated condition" is a disorder which may be prevented, partially alleviated or cured by the administration of an $I_{Kur}$ blocker. The Kv1.5 gene is known to be expressed in stomach tissue, intestinal/colon tissue, the pulmonary artery, and pancreatic beta cells. Thus, administration of an $I_{Kur}$ blocker can provide useful treatment for disorders such as: reflux esauphagitis, functional dispepsia, constipation, asthma, and diabetes. Additionally, Kv1.5 is known to be expressed in the anterior pituitary. Thus, administration of an $I_{Kur}$ blocker can stimulate growth hormone secretion. $I_{Kur}$ inhibitors can additionally be useful in the treatment of cell proliferative disorders such as leukemia, and autoimmune diseases such as rheumatoid arthritis and transplant rejection.

The present invention thus provides methods for the prevention or treatment of one or more of the aforementioned disorders, comprising the step of administering to a subject in need thereof an effective amount of at least one compound of the formula 1. Other therapeutic agents such as those described herein may be employed with the inventive compounds in the present methods. In the methods of the present invention, such other therapeutic agent(s) may be administered prior to, simultaneously with or following the administration of the compound(s) of the present invention.

The present invention also provides pharmaceutical compositions comprising at least one of the compounds of the formula I or salts thereof capable of preventing or treating one or more of the aforementioned disorders in an amount effective therefor, and a pharmaceutically acceptable vehicle or diluent. The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the formula I may be administered by any suitable means, for example, orally, such as in the form of tablets, capsules, granules or powders; sublingually; bucally; parenterally, such as by subcutaneous, intravenous, intramuscular, or intrasternal injection or infusion techniques (e.g., as sterile injectable aqueous or non aqueous solutions or suspensions); nasally such as by inhalation spray; topically, such as in the form of a cream or ointment; or rectally such as in the form of suppositories; in dosage unit formulations containing non toxic, pharmaceutically acceptable vehicles or diluents. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. In the case where the compounds of formula I are being administered to prevent or treat arrhythmias, the compounds may be administered to achieve chemical conversion to normal sinus rhythm, or may optionally be used in conjunction with electrical cardioconversion.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The compounds of formula I may also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non toxic, parenterally acceptable diluents or solvents, such as mannitol, 1,3 butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, a suitable non irritating excipient, such as cocoa butter, synthetic glyceride esters or polyethylene glycols, which are solid at ordinary temperatures but liquify and/or dissolve in the rectal cavity to release the drug.

Exemplary compositions for topical administration include a topical carrier such as Plastibase (mineral oil gelled with polyethylene).

The effective amount of a compound of the present invention may be determined by one of ordinary skill in the art, and includes exemplary dosage amounts for an adult human of from about 0.001 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to the aforementioned disorders.

The compounds of the present invention may be employed alone or in combination with each other and/or other suitable therapeutic agents useful in the treatment of the aforementioned disorders or other disorders, including: other antiarrhythmic agents such as Class I agents (e.g., propafenone), Class II agents (e.g., carvadiol and propranolol), Class III agents (e.g., sotalol, dofetilide, amiodarone, azimilide and ibutilide), Class IV agents (e.g., diltiazem and verapamil), 5HT antagonists (e.g., sulamserod, serraline and tropsetron), and dronedarone; calcium channel blockers (both L-type and T-type) such as diltiazem, verapamil, nifedipine, amlodipine and mybefradil; Cyclooxygenase inibitors (i.e., COX-1 and/ or COX-2 inhibitors) such as aspirin, indomethacin, ibuprofen, piroxicam, naproxen, Celebrex™, Vioxx™ and NSAIDs; anti-platelet agents such as GPIIb/IIIa blockers (e.g., abciximab, eptifibatide and tirofiban), P2Y12 antagonists (e.g., clopidogrel, cangrelor, ticlopidine and CS-747), P2Y1 antagonists, thromboxane receptor antagonists (e.g., ifetroban), aspirin, and PDE-III inhibitors (e.g., dipyridamole) with or without aspirin; diuretics such as chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetamide, triamtrenene, amiloride, and spironolactone; anti-hypertensive agents such as alpha adrenergic blockers, beta adrenergic blockers, calcium channel blockers, diuretics, renin inhibitors, ACE inhibitors, (e.g., captropril, zofenopril, fosinopril, enalapril, ceranopril, cilazopril, delapril, pentopril, quinapril, ramipril, lisinopril), A II antagonists (e.g., losartan, irbesartan, valsartan), ET antagonists (e.g. sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP- ACE inhibitors) (e.g., omapatrilat and gemopatrilat), nitrates, and combinations of such anti-hypertensive agents; anti-thrombotic/thrombolytic agents such as tissue plasminogen activator (tPA), recombinant tPA, tenecteplase (TNK), lanoteplase (nPA), factor VIIa inhibitors, factor Xa inhibitors (such as razaxaban), XIa inhibitors, thromin inibitors (e.g., hirudin and argatroban), PAI-1 inhibitors (i.e., inactivators of tissue plasminogen activator inhibitors), α2-antiplasmin inhibitors, streptokinase, urokinase, prourokinase, anisoylated plasminogen streptokinase activator complex, and animal or salivary gland plasminogen activators; anticoagulants such as warfarin and heparins (including unfractionated and low molecular weight heparins such as enoxaparin and dalteparin); HMG-CoA reductase inhibitors such as pravastatin lovastatin, atorvastatin, simvastatin, NK-104 (a.k.a. itavastatin, or nisvastatin or nisbastatin) and ZD-4522 (a.k.a. rosuvastatin, or atavastatin or visastatin); other cholesterol/lipid lowering agents such as squalene synthetase inhibitors, fibrates, and bile acid sequestrants (e.g., questran); antipoliferative agents such as cyclosporin A, taxol, FK 506, and adriamycin; antitumor agents such as taxol, adriamycin, epothilones, cisplatin and carboplatin; anti-diabetic agents such as biguanides (e.g. mefformin), glucosidase inhibitors (e.g. acarbose), insulins, meglitinides (e.g. repaglinide), sulfonylureas (e.g. glimepiride, glyburide and glipizide), biguanide/glyburide combinations (i.e,. glucovance), thiozolidinediones (e.g. troglitazone, rosiglitazone and pioglitazone), PPAR-gamma agonists, aP2 inhibitors, and DP4 inhibitors; thyroid mimetics (including thyroid receptor antagonists) (e.g., thyrotropin, polythyroid, KB-130015, and dronedarone); Mineralocorticoid receptor antagonists such as spironolactone and eplerinone; growth hormone secretagogues; anti-osteoporosis agents (e.g., alendronate and raloxifene); hormone replacement therapy agents such as estrogen (including conjugated estrogens in premarin), and estradiol; antidepressants such as nefazodone and sertraline; antianxiety agents such as diazepam, lorazepam, buspirone, and hydroxyzine pamoate; oral contraceptives; anti-ulcer and gastroesophageal reflux disease agents such as famotidine, ranitidine, and omeprazole; anti-obesity agents such as orlistat; cardiac glycosides including digitalis and ouabain; phosphodiesterase inibitors including PDE III inhibitors (e.g. cilostazol), and PDE V inhibitors (e.g., sildenafil); protein tyrosine kinase inhibitors; steroidal anti-inflammatory agents such as prednisone, and dexamethasone; and other anti-inflammatory agents such as enbrel. The combinations can be co-formulated or in the form of kits packaged to provide appropriate dosages for co-administration.

The above other therapeutic agents, when employed in combination with the compounds of the present invention, may be used, for example, in those amounts indicated in the Physicians' Desk Reference (PDR) or as otherwise determined by one of ordinary skill in the art.

Assays to determine the degree of activity of a compound as an $I_{Kur}$ inhibitor are well known in the art and are described in references such as *J. Gen. Physiol.* April; 101(4): 513-43, and *Br. J. Pharmacol.* 1995 May; 115(2): 267-74. It has been shown in animal models that active drug compounds resulting from the prodrugs of the invention prolong the myocardial refractoriness, i.e. the effective refractory period (ERP), in the atrium, for example in the range of up to 60% extension of ERP based on dosage of the compounds of the invention ranging from 0.1 to about 100 mg/kg of subject weight.

Assays to determine the degree of activity of a compound as an inhibitor of other members of the Kv1 subfamily are also well known in the art. For example, inhibition of Kv1.1, Kv1.2 and Kv1.3 can be measured using procedures described by.

Grissmer S, et al., *Mol Pharmacol* 1994 June; 45(6): 1227-34. Inhibition of Kv1.4 can be measured using procedures described by Petersen K R, and Nerbonne J M, *Pflugers Arch* 1999 February; 437(3): 381-92. Inhibition of $Kv_{1.6}$ can be measured using procedures described by Bowlby M R, and Levitan I B, *J Neurophysiol* 1995 June; 73(6): 2221-9. And inhibition of Kv1.7 can be measured using procedures described by Kalman K, et al., *J Biol Chem* 1998 Mar. 6; 273(10): 5851-7.

Methods of Preparation

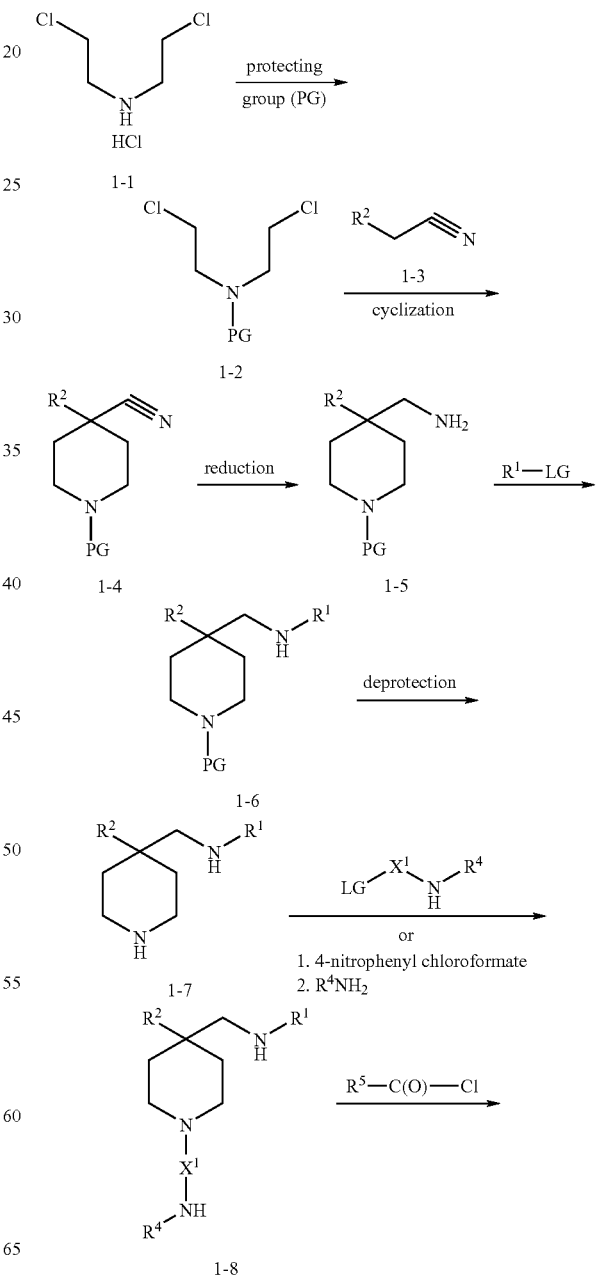

-continued

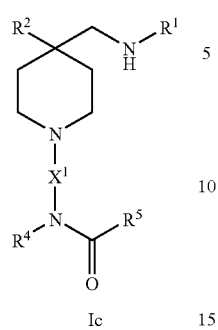

Compounds of formula I having the structure of formula Ic, wherein $X^1$, $R^2$, $R^4$ and $R^5$ are defined as above, and $R^1$ is selected from —C(=O)aryl, —C(=O)heteroaryl, aryl, heteroaryl, —CH$_2$-aryl, or —CH$_2$-heteroaryl, can be prepared as described in Scheme 1. Protection of compound 1-1 gives compound 1-2. One skilled in the art will recognize that a variety of nitrogen protecting groups are known in the literature. In this example, preferred protecting groups include the benzyl (Bn), tert-butoxycarbonyl (Boc) and carbobenzyloxy (CBz) groups. Condensation of compound 1-2 with nitrile compound 1-3 gives the protected piperidine compound 1-4. The nitrile group of compound 1-4 may be reduced using various methods, including treatment with lithium aluminum hydride or hydrogenation in the presence of platinum (IV) oxide, to provide the primary amine compound 1-5. Reaction of compound 1-5 with $R^1$-LG, wherein $R^1$ is defined as hereinabove and LG is any suitable leaving group, provides compound 1-6. In this example, suitable leaving groups (LG) include a halogen or triflaite. Deprotection of compound 1-6 provides the piperidine compound 1-7. Reaction of compound 1-7 with LG-$X^1$—N(H)$R^4$, wherein $X^1$ and $R^4$ are defined as hereinabove, provides compound 1-8. Synthesis of other active drug species (as shown above for compound 1-8) having different ring structures and substitution, are reflected in co-pending U.S. Application No. U.S. 20040110793A1, the entire disclosure of which is herein incorporated by reference. In the foregoing scheme, suitable leaving groups (LG) include —NH$_2$ or imidazole when $X^1$ is —SO$_2$— or, LG can also be —SMe or OPh when $X^1$ is C=N(CN), C=N(NO$_2$) or C=N(SO$_2$alkyl). In addition, reaction of compound 1-7 with 4-nitrophenyl chloroformate followed by treatment with an amine $R^4$NH$_2$ provides compound 1-8 where $X^1$ is —CO—. Acylation of compound 1-8 with $R^5$—C(O)—Cl, wherein $R^5$ is defined as hereinabove, provides the compound of formula Ic. Alternatively, compound 1-4 can be prepared according to Scheme 1a from compound 1-9 by protecting the N group followed by coupling with $R^2$-LG, wherein $R^2$ is defined as hereinabove and LG is a suitable leaving group (e.g. halide, triflate, etc.) in the presence of a base.

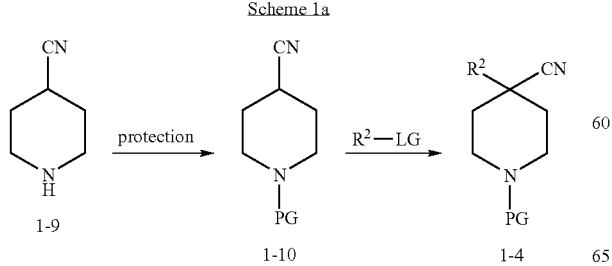

EXAMPLES

The following non-limiting examples are illustrative of the invention.

Example 1

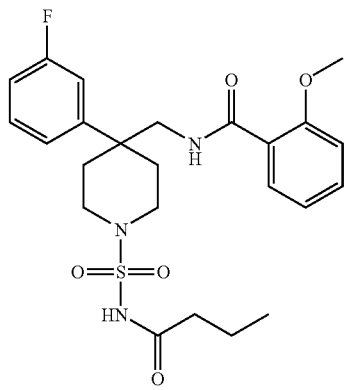

N-[1-Butyrylsulfamoyl-4-(3-fluoro-phenyl)-piperidin-4-ylmethyl]-2-methoxy-benzamide N-[1-Butyrylsulfamoyl-4-(3-fluoro-phenyl)-piperidin-4-ylmethyl]-2-methoxy-benzamide was synthesized according to Scheme 2.

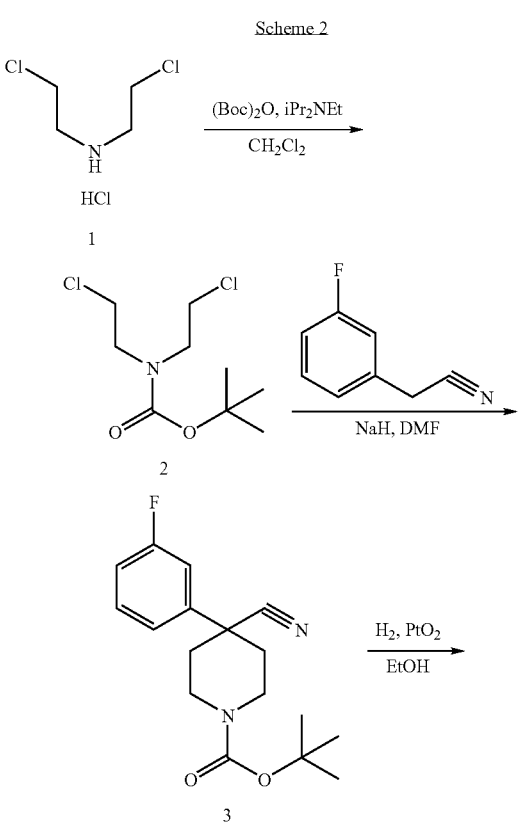

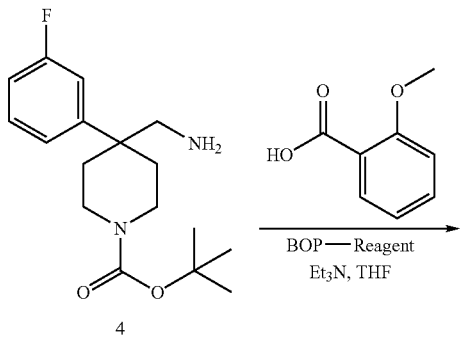

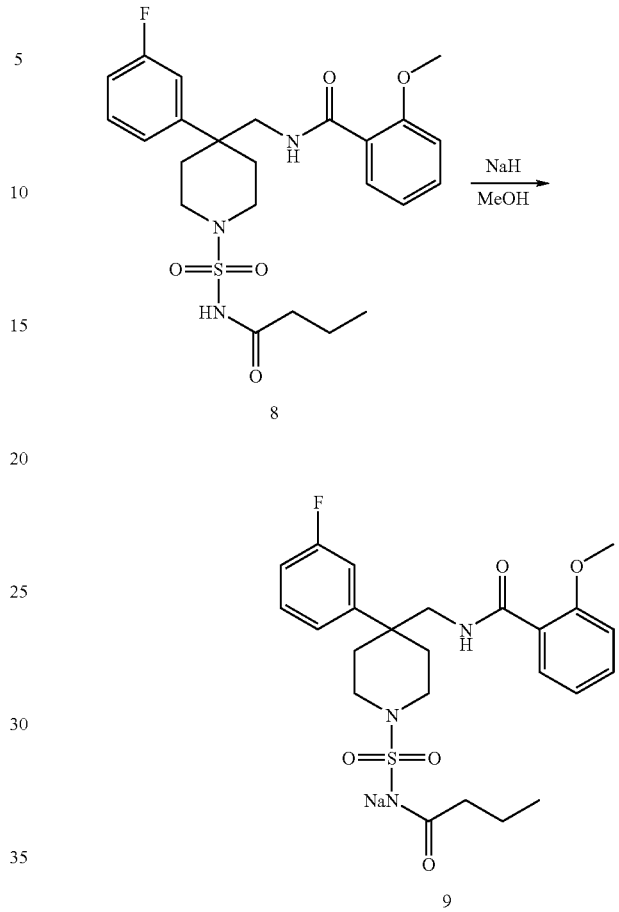

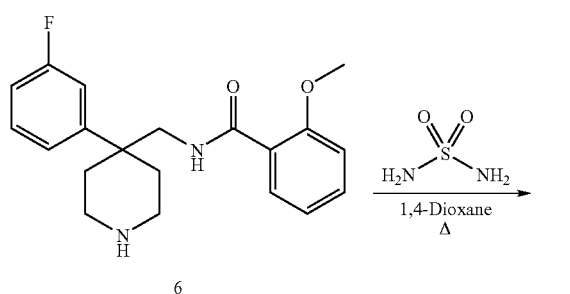

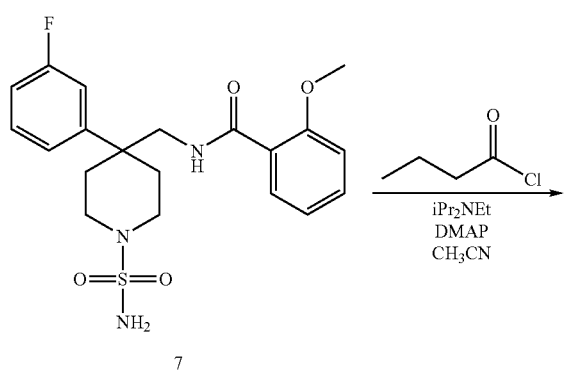

Compound 1 is commercially available, for example from Aldrich, St. Louis, Mo. The preparation of each of Compounds 2-9 is described below.

Compound 2: A solution of compound 1 (5.0 g, 28.0 mmol) in 100 mL of dichloromethane was treated di-tert-butyl dicarbonate (6.1 g, 28.0 mmol) and diisopropylethylamine (10.7 mL, 61.6 mmol). The reaction mixture was stirred at room temperature overnight. The reaction mixture was diluted with diethyl ether (300 mL) and washed with 1 N hydrochloric acid (2×100 mL), saturated sodium bicarbonate (100 mL), water (100 mL) and saturated sodium chloride (100 mL). The organic layer was dried over sodium sulfate and concentrated. The residue was purified using flash chromatography on silica gel using 9:1 hexane:diethyl ether as the eluent to give compound 2 (3.46 g, 51% yield) as a colorless oil.

Compound 3: Sodium hydride (1.9 g, 79.0 mmol) was suspended in dimethylformamide (30 mL) and cooled to 0° C. 3-Fluorophenylacetonitrile (2.61 g, 19.3 mmol) was slowly added followed by a solution of compound 2 (3.68 g, 15.2 mmol) in dimethylformamide (30 mL). The reaction was stirred at 0° C. for 0.5 hours then allowed to warm to room temperature and stirred overnight. The reaction mixture was poured onto ice and extracted with ethyl acetate (200 mL). The aqueous layer was extracted with ethyl acetate (2×200 mL). The organic layers were combined and washed with 10% lithium chloride (2×100 mL), dried over sodium sulfate, filtered and concentrated. The residue was purified using flash chromatography on silica gel using 9:1 hexane:ethyl acetate as the eluent to give compound 3 (4.04 g, 87% yield) as a yellow oil. LRMS m/z 305 (M+H)$^+$. $^1$H NMR (CDCl$_3$) δ 1.48 (9H, s), 1.92 (2H, td, J=4.3, 13.1), 2.05 (2H, t, J=10.2), 3.19 (2H, t, J=12.4), 4.29 (2H, d, J=13.7), 7.01-7.45 (4H, m).

Compound 4: A solution of compound 3 (4.04 g, 13.27 mmol) in 50 mL of 15% acetic acid/ethanol was treated with platinum (IV) oxide (0.210 g, 0.925 mmol) and hydrogenated under 60 psi H$_2$ (Parr Apparatus) for 48 h. The reaction mixture was filtered through a thick pad of celite and concentrated. To the concentrate was added 200 mL of diethyl ether and the organic solution was washed with 1 N sodium hydroxide (2×50 mL), dried over sodium sulfate, filtered and concentrated to give compound 4 (4.07 g, 100% yield). LRMS m/z 309 (M+H)$^+$.

Compound 5: A solution of compound 4 (8.34 g, 27.04 mmol) in 212 mL of tetrahydrofuran was treated with o-anisic acid (0.270 g, 1.94 mmol), benzotriazole-1-yl-oxy-tris-(dimethylamino)-phosphoniumhexafluorophosphate (BOP-reagent) (11.96 g, 27.04 mmol) and triethylamine (3.8 mL, 27.04 mmol). The reaction mixture stirred for 2 h at room temperature. The reaction mixture was concentrated and diluted with methylene chloride (200 mL). The organic layer was washed with water (3×150 mL) and saturated sodium chloride (150 mL) and dried over sodium sulfate. After filtration, the solvent was evaporated and the crude product was purified using column chromatography on silica gel using 2:1 ethyl acetate:hexane as the eluent to give compound 5 (9.28 g, 77% yield). LRMS m/z 443 (M+H)$^+$.

Compound 6: Compound 5 (0.691 g, 1.61 mmol) was suspended in tetrahydrofuran (5 mL), 4N hydrochloric acid in 1,4-dioxane (5 mL) was added and the reaction was stirred overnight at room temperature. The reaction mixture was concentrated and partitioned between water (15 mL) and diethyl ether (2×15 mL). The organic layer was discarded and 6 N sodium hydroxide was added to basify the aqueous layer. The aqueous layer was extracted with dichloromethane (3×20 mL) and the combined organic layers were dried over sodium sulfate, filtered and concentrated. Compound 6 (471 mg, 89% yield) was obtained as a yellow solid.

LRMS m/z 343 (M+H)$^+$.

Compound 7: A solution of compound 6 (5.23 g, 15.27 mmol) in 1,4-dioxane (102 mL) was treated with sulfamide (2.94 g, 30.55 mmol) and the reaction mixture was heated at reflux overnight. After cooling to room temperature, additional sulfamide (1.47 g, 15.27 mmol) was added and the reaction mixture was heated at reflux for an additional 6 h. After cooling to room temperature the reaction mixture was concentrated, diluted with dichloromethane (200 mL), and washed with 1 N hydrochloric acid, water and saturated aqueous sodium chloride. The organic layer was dried over sodium sulfate, filtered and concentrated. The crude product was purified by column chromatography on silica gel using 3:1 ethyl acetate:hexane as the eluent to give compound 7 (5.23 grams, 81% yield) as a white foam. LRMS m/z 422 (M+H)$^+$. $^1$H NMR (CDCl$_3$) δ 2.08-2.21 (4H, m), 3.19-3.27 (2H, m), 3.35-3.43 (2H, m), 3.65 (3H, s), 3.76 (2H, d, J=6.2), 4.42 (2H, s), 6.88 (1H, d, J=8.4), 7.01-7.10 (3H, m), 7.16 (1H, J=8.0), 7.38-7.45 (2H, m), 7.62 (1H, s), 8.16 (1H, dd, J=7.9, J=7.85).

Compound 8 (title compound): A solution of compound 7 (0.37 g; 0.88 mmol) in acetonitrile was treated with diisopropylethylamine (0.3 mL; 1.72 mmol), 4-dimethylaminopyridine (0.11 g; 0.9 mmol) and butyryl chloride (0.36 mL; 3.44. mmol). The reaction mixture was heated at 80° C. for 2 h and then allowed to stir at room temperature overnight. The solvent was removed by rotary evaporation and the residue was treated with ethyl acetate and 0.5 N HCl. The organic layer was separated, washed with aqueous saturated sodium chloride, dried over sodium sulfate, filtered and concentrated. The crude product was purified by automated column chromatography on silica gel using a gradient of 45% ethyl acetate in hexane to 100% ethyl acetate to give the title compound (0.35 g; 81% yield) as a white foam.

LRMS m/z 492 (M+H)$^+$. $^1$H NMR (CDCl$_3$) δ 8.35 (s, 1H), 8.14 (dd, J=2.1 and 7.8 Hz, 1H), 7.61 (t, J=6.0 Hz, 1H), 7.44-7.36 (m, 2H), 7.14 (d, J=7.8 Hz, 1H), 7.07-6.98 (m, 3H), 6.88 (d, J=8.4 Hz, 1H), 3.72 (d, J=6.0 Hz, 2H), 3.65 (s, 3H), 3.62-3.57 (m, 2H), 3.40-3.32 (m, 2H), 2.24 (t, J=7.5 Hz, 2H), 2.20-2.15 (m, 2H), 2.06-2.00 (m, 2H), 1.63 (sextet, J=7.5 Hz, 2H), 0.91 (t, J=7.5 Hz, 3H).

Compound 9: A solution of compound 8 (0.082 g; 0.17 mmol) in anhydrous methanol was treated with sodium hydride (0.005 g; 0.21 mmol) and stirred at room temperature for 0.5 h. The solvent was removed by rotary evaporation to provide the sodium salt compound 9 as a white solid in quantitative yield. $^1$H NMR (D$_2$O) δ 8.31 (s, 1H), 7.47 (d, J=8.1 Hz, 1H), 7.34-7.22 (m, 2H), 7.08-7.00 (m, 2H), 6.92-6.85 (m, 3H), 3.53 (s, 3H), 3.37 (s, 2H), 3.27-3.21 (m, 2H), 2.75 (broad t, J=10.2 Hz, 2H), 2.17-2.12 (m, 2H), 1.92 (t, J=7.5 Hz, 2H), 1.77-1.70 (m, 2H), 1.29 (sextet, J=7.5 Hz, 2H), 0.63 (t, J=7.5 Hz, 3H).

Example 2

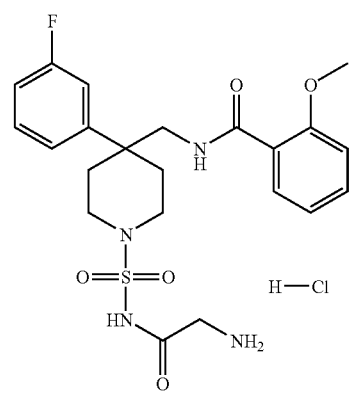

N-[1-(2-Amino-acetylsulfamoyl)-4-(3-fluoro-phenyl)-piperidin-4-ylmethyl]-2-methoxy-benzamide-hydrochloride N-[1-(2-Amino-acetylsulfamoyl)-4-(3-fluoro-phenyl)-piperidin-4-ylmethyl]-2-methoxy-benzamide-hydrochloride was synthesized according to Scheme 3.

Scheme 3

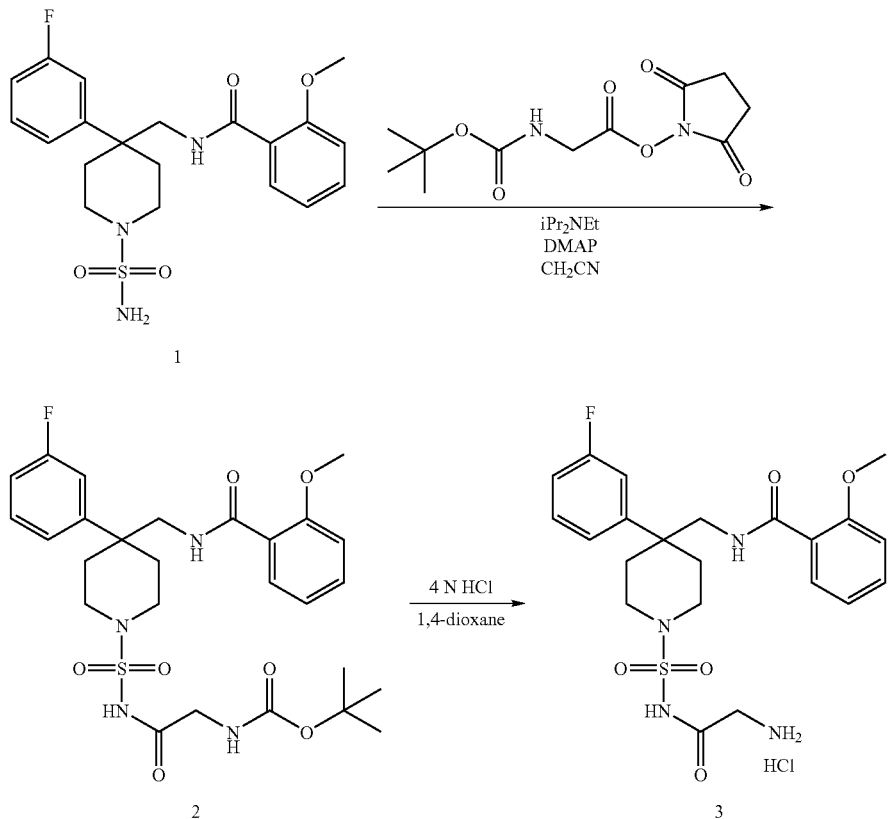

Compound 1: Compound 1 of this Example was prepared as described in Example 1.

Compound 2: A solution of compound 1 (0.32 g; 0.75 mmol) in acetonitrile (10 mL) was treated with diisopropylethylamine (0.26 mL; 1.5 mmol), 4-dimethylaminopyridine (0.11 mmol; 0.9 mmol) and Boc-glycine N-hydroxysuccinimide ester (0.43 g; 1.6 mmol) and the reaction mixture was heated at 80° C. for 48 h. The reaction mixture was cooled to room temperature, additional diisopropylethylamine (0.20 mL; 1.1 mmol) and Boc-glycine N-hydroxysuccinimide ester (0.46 g; 1.7 mmol) was added and the reaction mixture was heated to 80° C. for an additional 3 h. The solvent was removed by rotary evaporation and the residue was treated with ethyl acetate and 0.5 N HCl. The organic layer was separated, washed with aqueous saturated sodium chloride, dried over sodium sulfate, filtered and concentrated. The crude product was purified by automated column chromatography on silica gel using a gradient of 50% ethyl acetate in hexane to 100% ethyl acetate to give the title compound (0.40 g; 92% yield) as a white foam. LRMS m/z 579 (M+H)+.

Compound 3 (title compound): To a solution of compound 2 (0.29 g; 0.61 mmol) in anhydrous tetrahydrofuran (2 mL) was added dropwise 2 mL of 4 N hydrogen chloride in 1,4-dioxane. The reaction was allowed to stir at room temperature for 2 h. The solvent was removed by rotary evaporation and the residue was dissolved in warm isopropanol. Upon cooling to 0° C., a precipitate formed that was collected to give the title compound (0.15 g; 58%) as a white solid. LRMS m/z 479 (M+H)+.

Example 3

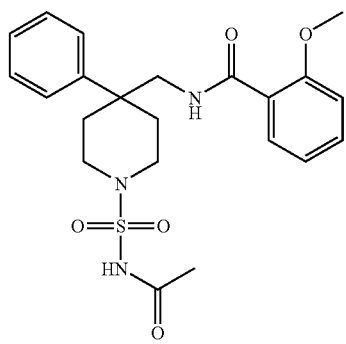

N-(1-Acetylsulfamoyl-4-phenyl-piperidin-4-ylmethyl)-2-methoxy-benzamide

Example 3 was prepared using a method analogous to that used for the preparation of Example 1.

The Compounds of Examples 1 and 2, as well as compounds of Example 3 (represented below by formula Id), were evaluated to observe the rate of metabolism of the compounds as prodrugs and the resulting bioavailability of the active drug ingredient represented by Formula Ic or 1d after oral administration in feeding studies

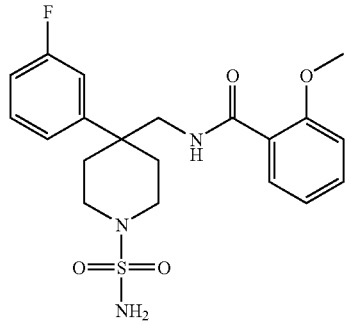

Ic

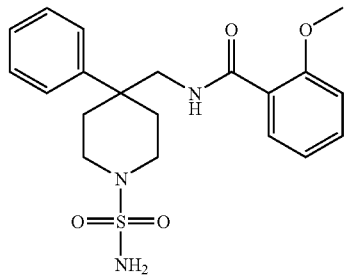

Id

Male Sprague-Dawley rats were dosed PO with 10 mg/kg of the prodrug in 1:2:2 ethanol:PEG400:$H_2O$, and blood plasma concentration of the prodrug and the active drug compound measured over time.

The results are summarized in Table 1.

TABLE 1

| Example | Prodrug compound | Time post PO administration at 10 mg/kg (hours) | Plasma concentration of prodrug (μM) | Plasma concentration of drug compounds 1c/1d (μM) |
| --- | --- | --- | --- | --- |
| 4 | | 0.25<br>2 | 0.1<br>0.01 | 1.8<br>3.3 |
| 5 | | 0.25<br>2.0 | 0.001<br>0.001 | 0.174<br>0.08 |

TABLE 1-continued

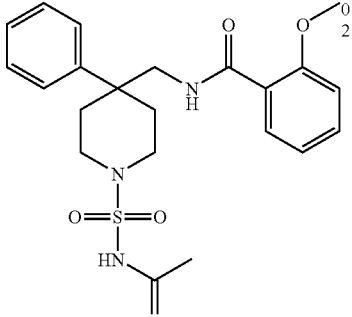

| | | 0.25 | 0.49 | 1.73 |
| --- | --- | --- | --- | --- |
| 6 | | 2.0 | 0.11 | 0.89 |

The results indicated rapid and efficient metabolism of the compounds of the invention to provide the active drug compound.

Additional examples of prodrug compounds of the invention which could be prepared using methodology described in Scheme 1, Scheme 2 and Scheme 3 are presented in Table 2. The synthesis of the corresponding active drug species (e.g.; compound 1-8 in Scheme 1, compound 7 in Scheme 2 and compound 1 in Scheme 3) is described in U.S. Application No. U.S. 20040110793A1, herein incorporated by reference.

| Example | Prodrug compound |
| --- | --- |
| 7 | 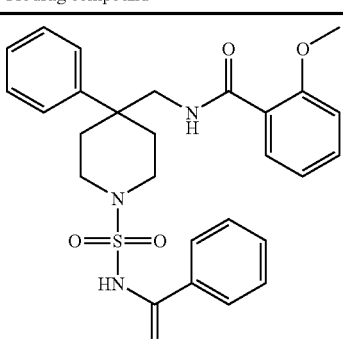 |
| 8 | 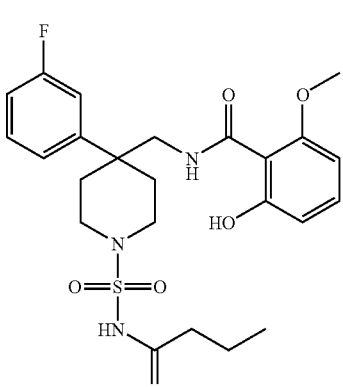 |

-continued

| Example | Prodrug compound |
| --- | --- |
| 9 | 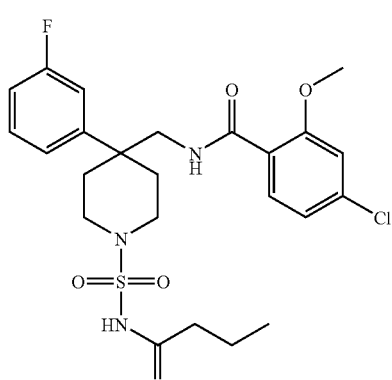 |
| 10 | 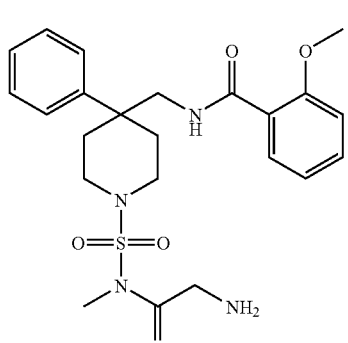 |

-continued
| Example | Prodrug compound |
|---|---|
| 11 | 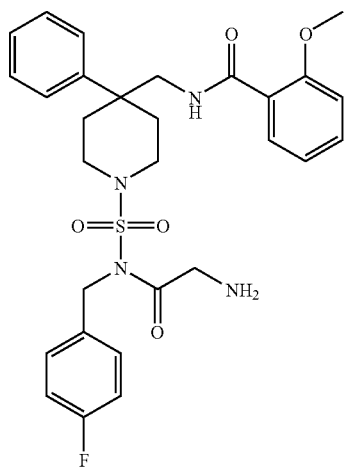 |
| 12 | 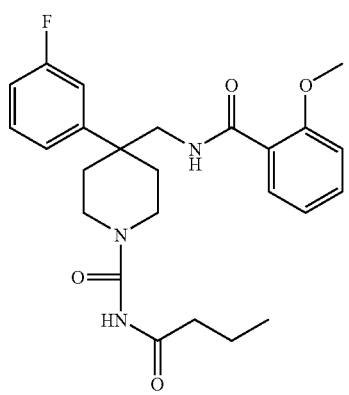 |
| 13 | 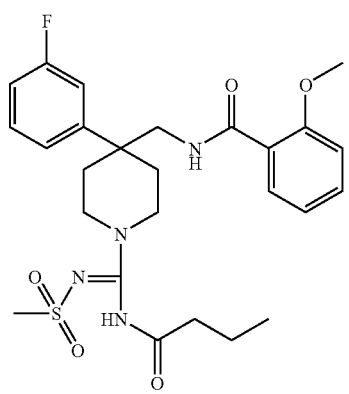 |
-continued
| Example | Prodrug compound |
|---|---|
| 14 | 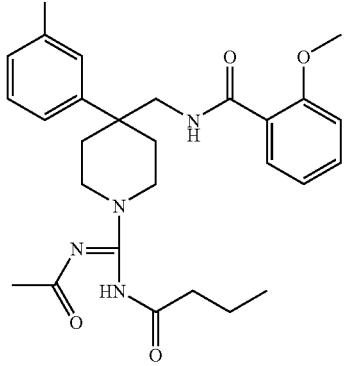 |
| 15 | 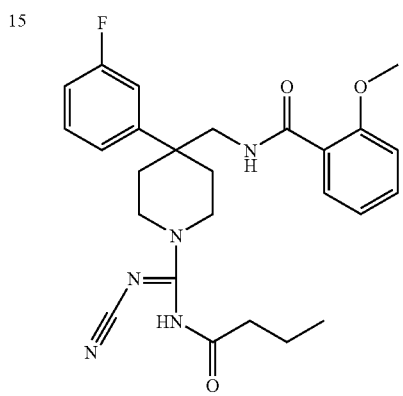 |
| 16 | 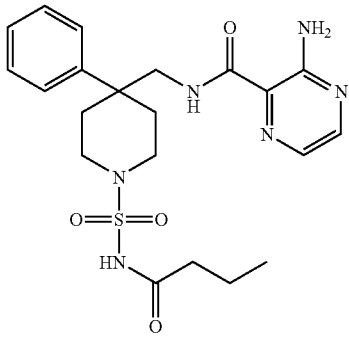 |

| Example | Prodrug compound |
|---|---|
| 17 | 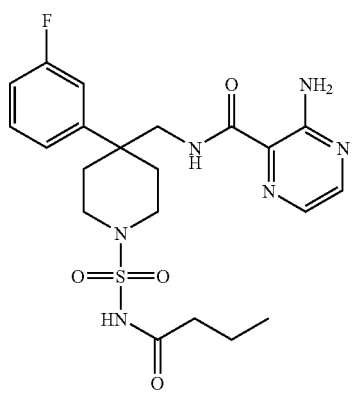 |
| 18 | 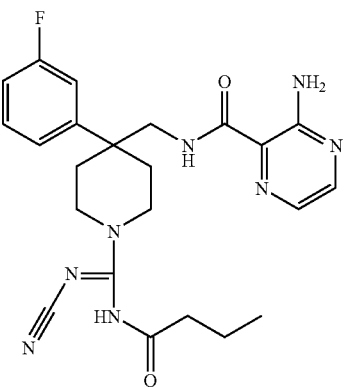 |
| 19 | 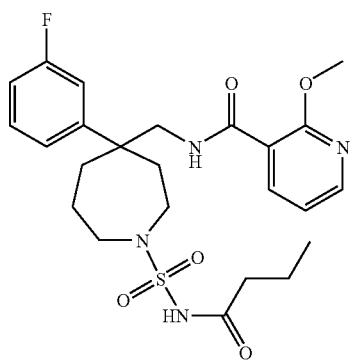 |
| 20 | 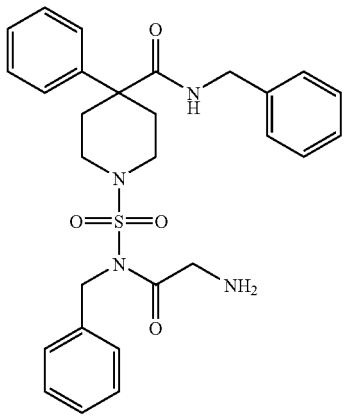 |
| 21 | 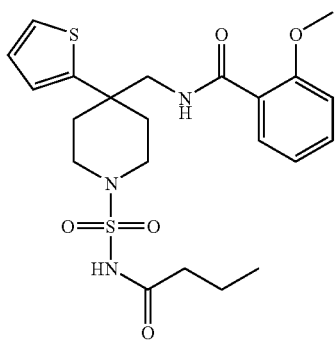 |
| 22 | 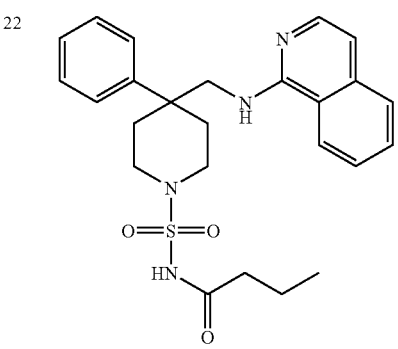 |

-continued

| Example | Prodrug compound |
|---|---|
| 23 | 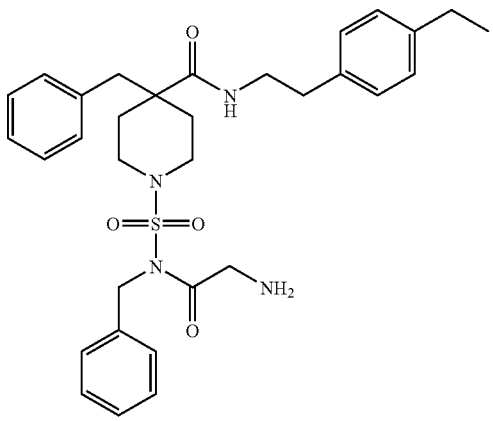 |

It is to be understood that the foregoing described embodiments and exemplifications are not intended to be limiting in any respect to the scope of the invention, and that the claims presented herein are intended to encompass all embodiments and exemplifications whether or not explicitly presented herein.

What is claimed is:

1. Compounds according to the formula I:

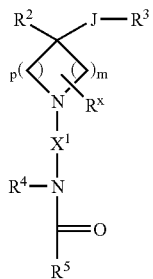

including enantiomers, diastereomers, and salts thereof, wherein
$X^1$ is selected from —$SO_2$— and —CO—
m and p are each 2;
J is a bond or $C_{1-4}$ alkylene;
$R^2$ is phenyl which may be optionally independently substituted with one or more groups $T^1$, $T^2$ or $T^3$;
$R^4$ is H;
$R^5$ is selected from $C_{1-3}$ alkyl and phenyl, each of which may be substituted with one or more groups $T^1$, $T^2$ or $T^3$;
$R^3$ is

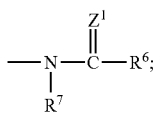

wherein $Z^1$ is selected from O, S or $NR^{13}$; where $R^{13}$ is hydrogen, alkyl, CN, $NO_2$, $SO_2$alkyl, $CO_2$alkyl or COalkyl;

$R^6$ is phenyl, piperazinyl or quinolinyl, each of which may be independently substituted with one or more groups $T^1$, $T^2$, or $T^3$;
$R^7$ is H or alkyl;
$R^X$ is H; and
$T^1$, $T^2$ and $T^3$ are each independently selected from
(1) hydrogen, alkyl, (hydroxy)alkyl and $CF_3$;
(2) —OH;
(3) —SH;
(4) halo,
(5) cyano, and
(6) nitro.

2. Compounds according to claim 1 wherein $R^2$ is phenyl substituted with one or more groups $T^1$, $T^2$ or $T^3$, at least one of which is F.

3. Compounds according to claim 1 wherein $R^5$ is $C_{1-3}$ alkyl.

4. Compounds according to formulae Ia:

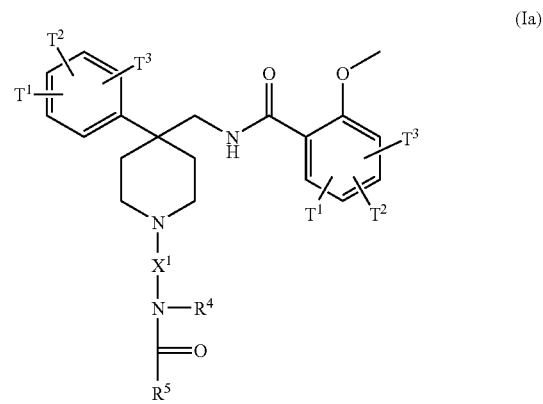

wherein $T^1$, $T^2$ and $T^3$ are each independently selected from hydrogen, F, Cl, Br, I or alkyl;
$X^1$ is selected from —$SO_2$— and —CO—;
$X^2$ is selected from —$C_{1-4}$alkyl, —O—$C_{1-4}$ alky and amino; and
$R^4$ and $R^5$ are as defined in claim 1.

5. A compound according to claim 1 which is N-[1-butyrylsulfamoyl-4-(3-fluoro-phenyl)-piperidin-4-ylmethyl]-2-methoxy-benzamide:

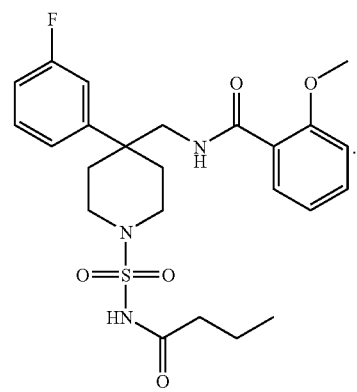

6. A compound according to claim 1 which is N-[1-(2-amino-acetylsulfamoyl)-4-(3-fluoro-phenyl)-piperidin-4-yl-methyl]-2-benzamide-hydrochloride:
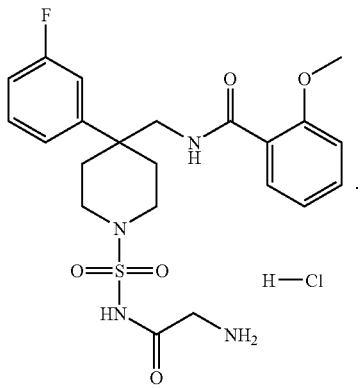
7. A compound according to claim 1 which is N-(1-acetyl-sulfamoyl-4-phenyl-pipendin-4-ylmethyl)-2-methoxy-benzamide:
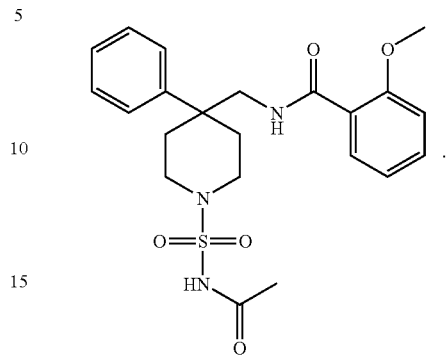
* * * * *